United States Patent [19]

Singh

[11] Patent Number: 4,699,984
[45] Date of Patent: Oct. 13, 1987

[54] PREPARATION OF INTERMEDIATES TO 6-FLUORO-7-(2,6-DIMETHYLPYRIDYL)-QUINOLINE CARBOXYLIC ACIDS AND COMPOUNDS

[75] Inventor: Baldev Singh, East Greenbush, N.Y.

[73] Assignee: Sterling Drug Inc., New York, N.Y.

[21] Appl. No.: 831,219

[22] Filed: Feb. 20, 1986

Related U.S. Application Data

[63] Continuation-in-part of Ser. No. 650,946, Sep. 17, 1984, abandoned.

[51] Int. Cl.$^4$ .................. C07D 213/55; C07D 213/38; C07D 213/26; C07B 43/04
[52] U.S. Cl. ..................................... 546/338; 546/329; 546/335; 546/346; 546/156; 546/89
[58] Field of Search ............... 546/346, 338, 329, 335, 546/89

[56] References Cited

U.S. PATENT DOCUMENTS 3,753,993  8/1973  Lesher et al. ..................... 546/156
3,907,808  9/1975  Lesher et al. ..................... 546/156

OTHER PUBLICATIONS

Streitwieser, A. et al., "Introduction to Organic Chemistry" (1976), Macmillan, p. 885.

*Primary Examiner*—Henry R. Jiles
*Assistant Examiner*—Dale A. Bjorkman
*Attorney, Agent, or Firm*—Thomas L. Johnson; Paul E. Dupont; Robert K. Bair

[57] ABSTRACT

Shown is the process which comprises heating 4-(2-fluorophenyl)-2,6-dimethyl-3,5-pyridinedicarboxylic acid to produce a mixture of 4-(2-fluorophenyl)-2,6-dimethylpyridine and 2,4-dimethyl-5H-[1]benzopyrano[3,4-c]pyridin-5-one, separating the components of said mixture and nitrating 4-(2-fluorophenyl)-2,6-dimethylpyridine to produce 4-(2-fluoro-5-nitrophenyl)-2,6-dimethylpyridine. Also shown are the 3-step synthesis of 4-(2-fluorophenyl)-2,6-dimethyl-3,5-pyridinedicarboxylic acid from 2-fluorobenzaldehyde and the five step synthesis of 1-ethyl-6-fluoro-1,4-dihydro-7-(2,6-dimethyl-4-pyridinyl)-4-oxo-3-quinolinecarboxylic acid, a highly potent antibacterial agent, starting with 4-(2-fluoro-5-nitrophenyl)-2,6-dimethylpyridine. Other intermediates shown in said five step synthesis include 3-(2,6-dimethyl-4-pyridinyl)-4-fluorobenzeneamine and diethyl 4-fluoro-3-(2,6-dimethyl-4-pyridinyl)anilinomethylenemalonate.

7 Claims, No Drawings

PREPARATION OF INTERMEDIATES TO 6-FLUORO-7-(2,6-DIMETHYLPYRIDYL)QUINOLINE CARBOXYLIC ACIDS AND COMPOUNDS

CROSS-REFERENCE TO RELATED APPLICATION

This application is a continuation-in-part of copending application Ser. No. 650,946, filed Sept. 17, 1984.

Copending Daum and Lesher U.S. patent application Ser. No. 651,121, filed Sept. 17, 1984, discloses and claims 1-ethyl-6-fluoro-1,4-dihydro-7-(2,6-dimethyl-4-pyridinyl)-4-oxo-3-quinolinecarboxylic acid, a highly potent antibacterial agent, and its preparation by nitrating the corresponding 6-desfluoro compound to produce the 6-nitro compound, reducing the 6-nitro compound to produce the 6-amino compound and converting the 6-amino compound via its 6-diazonium salt to produce said 6-fluoro compound, which is the ultimate product produced by the processes disclosed and claimed in the instant application.

BACKGROUND OF THE INVENTION

(1) Field of the Invention

This invention relates to an improved process for preparing 1-ethyl-6-fluoro-1,4-dihydro-7-(2,6-dimethyl-4-pyridinyl)-4-oxo-3-quinolinecarboxylic acid, a highly potent antibacterial agent having a broad spectrum of activity, to intermediates therefor and to their preparation.

(2) Information Disclosure Statement

Lesher and Carabateas U.S. Pat. No. 3,753,993, issued Aug. 21, 1973, shows as antibacterial agents 1-alkyl-1,4-dihydro-4-oxo-7-(pyridinyl)-3-quinolinecarboxylic acids. Illustrative of these compounds is 1-ethyl-1,4-dihydro-7-(2,6-dimethyl-4-pyridinyl)-4-oxo-3-quinolinecarboxylic acid (Example 6A, also known as Win 35,439), which was prepared stepwise as follows: first reacting 4-(3-aminophenyl)-2,6-dimethylpyridine with diethyl ethoxymethylenemalonate to produce diethyl 3-(2,6-dimethyl-4-pyridinyl)anilinomethylenemalonate (Example 6B), next heating the latter in an eutectic mixture of diphenyl and diphenyl ether (Dowtherm A) to produce ethyl 1,4-dihydro-7-(2,6-dimethyl-4-pyridinyl)-3-quinolinecarboxylate (Example 6C) and then heating said ester with ethyl iodide in dimethylformamide in the presence of anhydrous potassium carbonate to produce 1-ethyl-1,4-dihydro-7-(2,6-dimethyl-4-pyridinyl)-4-oxo-3-quinolinecarboxylic acid (Example 6A). Also shown in this patent as Example 1A is 1-ethyl-1,4-dihydro-4-oxo-7-(4-pyridinyl)-3-quinolinecarboxylic acid, now known generically as rosoxacin and also as Win 35,213.

Lesher and Carabateas U.S. Pat. No. 3,907,808, issued Sept. 23, 1975, show as antibacterial agents 1-alkyl-1,4-dihydro-4-oxo-5(or 6)-(halo, lower-alkyl or lower-alkoxy)-7-(pyridinyl)-3-quinolinecarboxylic acids. Illustrative of these compounds is 7-(3,5-dicarboxy-2,6-dimethyl-4-pyridinyl)-1-ethyl-6-fluoro-1,4-dihydro-4-oxo-3-quinolinecarboxylic acid (Example 57A), which was prepared in six steps starting with 2-fluoro-5-nitrobenzaldehyde as follows: (1) a mixture containing 2-fluoro-5-nitrobenzaldehyde, methyl acetoacetate, methanol and concentrated ammonium hydroxide was refluxed to produce dimethyl 4-(2-fluoro-5-nitrophenyl)-1,4-dihydro-2,6-dimethyl-3,5-pyridinedicarboxylate (Example 57B); (2) oxidizing the product of Example 57B by heating it with 4N nitric acid to produce dimethyl 4-(2-fluoro-5-nitrophenyl)-2,6-dimethyl-3,5-pyridinedicarboxylate (Example 57C); (3) catalytically hydrogenating Example 57C to produce dimethyl 4-(5-amino-2-fluorophenyl)-2,6-dimethyl-3,5-pyridinedicarboxylate (Example 57D); (4) reacting Example 57D with diethyl ethoxymethylenemalonate to produce 3-(3,5-dicarbomethoxy)-2,6-dimethyl-4-pyridinyl)-4-fluoroanilinomethylenemalonate (Example 57E); (5) heating Example 57E in Dowtherm A to produce ethyl 7-(3,5-dicarbomethoxy-2,6-dimethyl-4-pyridinyl)-6-fluoro-1,4-dihydro-4-oxo-3-quinolinecarboxylate (Example 57F); and, (6) heating Example 57F with ethyl iodide in dimethylformamide in the presence of anhydrous potassium carbonate and saponifying the resulting compound to produce 7-(3,5-dicarboxy-2,6-dimethyl-4-pyridinyl)-1-ethyl-6-fluoro-1,4-dihydro-4-oxo-3-quinolinecarboxylic acid (Example 57A). Example 56F of this patent shows the conversion of 4-(2-methoxy-5-nitrophenyl)-2,6-dimethyl-3,5-pyridinedicarboxylic acid to 4-(2-methoxy-5-nitrophenyl)-2,6-dimethylpyridine by heating it in Dowtherm A. Also, Example 64C shows the conversion of 7-(3,5-dicarboxy-2,6-dimethyl-4-pyridinyl)-1-ethyl-1,4-dihydro-6-methyl-4-oxo-3-quinolinecarboxylic acid to 7-(2,6-dimethyl-4-pyridinyl)-1-ethyl-1,4-dihydro-6-methyl-4-oxo-3-quinolinecarboxylic acid by heating it in diethyl phthalate at 240°-255° C.

SUMMARY OF THE INVENTION

In a process aspect, the invention resides in the process which comprises heating 4-(2-fluorophenyl)-2,6-dimethyl-3,5-pyridinedicarboxylic acid to produce a mixture of 4-(2-fluorophenyl)-2,6-dimethylpyridine and 2,4-dimethyl-5H-[1]benzopyrano[3,4-c]pyridin-5-one. separating the components of said mixture, and nitrating the 4-(2-fluorophenyl)-2,6-dimethylpyridine thus obtained to produce 4-(2-fluoro-5-nitrophenyl)-2,6-dimethylpyridine. As shown hereinbelow, 4-(2-fluoro-5-nitrophenyl)-2,6-dimethylpyridine is useful as an intermediate to prepare in very good yield the corresponding 4-(5-amino-2-fluorophenyl)-2,6-dimethylpyridine which is converted in four steps (all in very good yields) to 1-ethyl-6-fluoro-1,4-dihydro-7-(2,6-dimethyl-4-pyridinyl)-4-oxo-3-quinolinecarboxylic acid, a highly potent antibacterial agent having activity against a broad spectrum of microorganisms. The overall process provides an improved and convenient means for preparing large scale quantities of said antibacterial agent.

Other process aspects of the invention resides in the process which comprises heating 4-(2-fluorophenyl)-2,6-dimethyl-3,5-pyridinecarboxylic acid to produce above-said mixture of compounds and separating the components of the mixture and, also, in the process which comprises nitrating 4-(2-fluorophenyl)-2,6-dimethylpyridine to produce 4-(2-fluoro-5-nitrophenyl)-2,6-dimethylpyridine.

In a composition of matter aspect, the invention resides in a compound of the formula I

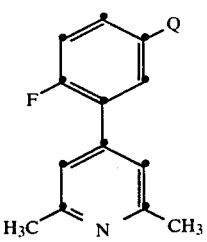

where Q is hydrogen, nitro, amino or NHCH=C(COOC$_2$H$_5$)$_2$, or acid-addition salt thereof. As noted above, these compounds are useful as key intermediates in the preparation of the highly potent antibacterial agent, 1-ethyl-6-fluoro-1,4-dihydro-7-(2,6-dimethyl-4-pyridinyl)-4-oxo-3-quinolinecarboxylic acid.

DETAILED DESCRIPTION INCLUSIVE OF PREFERRED EMBODIMENTS

The compounds of formula I are useful both in the free base form and in the form of acid-addition salts, and, both forms are within the purview of the invention. The acid-addition salts are an alternative and sometimes more convenient form for use; and in practice, use of the salt form inherently amounts to use of the base form. The acids which can be used to prepare the acid-addition salts of the compounds of formula I include preferably those which produce, when combined with the free base, pharmaceutically acceptable salts, that is, salts whose anions are relatively innocuous to animal organisms. Appropriate pharmaceutically acceptable salts within the scope of the invention are those derived from mineral acids such as hydrochloric acid, hydrobromic acid, sulfuric acid, phosphoric acid and sulfamic acid; and organic acids such as lactic acid, acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, lactate, acetate, citrate, tartrate, methanesulfonate, ethanesulfonate, benzenesulfonate, p-toluenesulfonate, cyclohexylsulfamate and quinate, respectively.

The acid-addition salts of said basic compound of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds of formula I is preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of formulas I were assigned on the basis of evidence provided by infrared, ultraviolet, nuclear magnetic resonance and mass spectra, by the correspondence of calculated and found values for the elemental analyses, and by their method of preparation.

The manner of making and using the instant invention will now be generally described so as to enable a person skilled in the art of pharmaceutical chemistry to make and use the same.

As shown hereinbelow in Example 1, the intermediate 4-(2-fluorophenyl)-2,6-dimethyl-3,5-pyridinedicarboxylic acid was prepared in very good yield by first adding concentrated aqueous ammonia to a mixture of 2-fluorobenzaldehyde and methyl acetoacetate in methanol to produce dimethyl 4-(2-fluorophenyl)-1,4-dihyro-2,6-dimethyl-3,5-pyridinedicarboxylate, oxidizing the 1,4-dihydro compound with 4N nitric acid to produce dimethyl 4-(2-fluorophenyl)-2,6-dimethyl-3,5-pyridinedicarboxylate and saponifying the latter ester by heating it with sodium hydroxide in aqueous methanol at about 60°–65° C. to produce 4-(2-fluorophenyl)-2,6-dimethyl-3,5-pyridinedicarboxylic acid.

Decarboxylation of 4-(2-fluorophenyl)-2,6-dimethyl-3,5-pyridinedicarboxylic acid to produce 4-(2-fluorophenyl)-2,6-dimethylpyridine was carried out conveniently by heating the dicarboxylic acid at about 240° C. to 300° C., preferably about 240°–255° C., in a suitable high boiling solvent, preferably by refluxing said dicarboxylic acid in a eutectic mixture of diphenyl and diphenyl ester (Dowtherm A) whereupon there resulted in the formation of 4-(2-fluorophenyl)-2,6-dimethylpyridine and varying amounts of 2,4-dimethyl-5H-[1]benzopyrano[3,4-c]pyridin-5-one as a side product, filtering off the side product from the cooled reaction mixture and then isolating the desired product. After removal of the side product, the desired product is isolated from the remaining reaction mixture by extracting it with an aqueous mineral acid, preferably HCl, making the acidic extract alkaline, preferably with aqueous ammonia, and extracting the product with a suitable solvent such as chloroform, ether or methylene dichloride. Other high boiling solvents that can be used in place of Dowtherm A are mineral oil, diethyl phthalate and the like. In using the preferred Dowtherm A, it was found that a greater proportion of the desired 4-(2-fluorophenyl)-2,6-dimethylpyridine and a lesser amount of the said side product were obtained by using a larger quantity of Dowtherm A. Use of recycled or previously used Dowtherm A decreased the yield of desired product.

The conversion of 4-(2-fluorophenyl)-2,6-dimethylpyridine to 4-(2-fluoro-5-nitrophenyl)-2,6-dimethylpyridine was carried out by adding a molar equivalent quantity or slight excess of a metal nitrate, preferably potassium nitrate, to 4-(2-fluorophenyl)-2,6-dimethylpyridine in excess concentrated sulfuric acid, keeping the reaction temperature below about 0° C., preferably between about −10° C. to −15° C., conveniently accomplished using an salt-ice bath. Alternatively, other alkali metal or alkaline earth metal nitrates, e.g., sodium nitrate or calcium nitrate, can be used in place of potassium nitrate.

4-(5-Amino-2-fluorophenyl)-2,6-dimethylpyridine, alternatively named 3-(2,6-dimethyl-4-pyridinyl)-4-fluorobenzeneamine (Example 4A), was prepared by catalytic hydrogenation of 4-(2-fluoro-5-nitrophenyl)-2,6-dimethylpyridine.

Reaction of 4-(5-amino-2-fluorophenyl)-2,6-dimethylpyridine with diethyl ethoxymethylenemalonate (EMME) produced diethyl 3-(2,6-dimethyl-4-pyridinyl)-4-fluoroanilinomethylenemalonate (Example 4B).

Preparation of 1-ethyl-6-fluoro-1,4-dihydro-7-(2,6-dimethyl-4-pyridinyl)-4-oxo-3-quinolinecarboxylic acid was then carried out by refluxing the EMME adduct of Example 4B in Dowtherm A to produce ethyl 6-fluoro-1,4-dihydro-7-(2,6-dimethyl-4-pyridinyl)-4-oxo-3-quinolinecarboxylate (Example 4C), ethylating the compound of Example 4C by heating it with ethyl iodide in dimethylformamide in the presence of anhydrous potassium carbonate to produce ethyl 1-ethyl-6-fluoro-1,4-dihydro-7-(2,6-dimethyl-4-pyridinyl)-4-oxo-3-quinolinecarboxylate (Example 4D) and hydrolyzing the compound of Example 4D by refluxing it in aqueous sodium hydroxide solution containing methanol to produce 1-ethyl 6-fluoro-1,4-dihydro-7-(2,6-dimethyl-4-pyridinyl)-4-oxo-3-quinolinecarboxylic acid (Example 4E).

The following examples will further illustrate the invention without, however, limiting it thereto.

EXAMPLE 1

A. Dimethyl 4-(2-fluorophenyl)-1,4-dihydro-2,6-dimethyl-3,5-pyridinedicarboxylate To a stirred solution containing 119 g of 2-fluorobenzaldehyde, 600 ml of methanol and 255 ml of methyl acetoacetate was added 200 ml of concentrated ammonium hydroxide whereupon an exothermic reaction ensued. The reaction mixture was stirred at ambient temperature for 30 minutes, next refluxed a few hours and then allowed to stand at room temperature overnight (about 15 hours). The yellow solid that crystallized was collected, washed with ether and dried in an oven at 50°-60° C. to yield 201 g of dimethyl 4-(2-fluorophenyl)-1,4-dihydro-2,6-dimethyl-3,5-pyridinedicarboxylate, m.p. 206°-208° C. Concentration of the mother liquor yielded another 26.4 g of the product, m.p. 204°-206° C. The total yield was 74%.

B. Dimethyl 4-(2-fluorophenyl)-2,6-dimethyl-3,5-pyridinedicarboxylate

To 600 ml of 90% nitric acid heated to about 70° C. was added with stirring over a period of 20 minutes 302.9 g of dimethyl 4-(2-fluorophenyl)-1,4-dihydro-2,6-dimethyl-3,5-pyridinedicarboxylate. The reaction mixture was heated on a steam bath for 1 hour and then allowed to cool with stirring for 2 hours. The reaction solution was then chilled and made basic with ammonium hydroxide solution. The resulting precipitate was collected, washed with water and dried in a vacuum oven at 75° C. to yield 302.8 g of yellow solid. The solid was slurried in water, collected, washed with water and dried in a vacuum oven at 65° C. to yield 273.7 g (90%) of product, m.p. 85°-88° C., which was used directly in the next step (Example 1C). A 20 g sample of the prodcut was dried at 70° C., recrystallized from n-hexane and dried in a vacuum oven at 65° C. to yield 15.9 g of dimethyl 4-(2-fluorophenyl)-2,6-dimethyl-3,5-pyridinedicarboxylate, m.p. 94°-96° C.

C. 4-(2-Fluorophenyl)-2,6-dimethyl-3,5-pyridinedicarboxylic Acid

A mixture containing 69 g of dimethyl 4-(2-fluorophenyl)-2,6-dimethyl-3,5-pyridinedicarboxylate, 300 ml of methanol and 100 ml of 35% aqueous sodium hydroxide solution was refluxed with stirring for 5 hours and then allowed to stand at room temperature overnight. The methanol was removed using a rotary evaporator and to the residual liquid was added 200 ml of water and filtered. The filtrate was acidifed with concentrated hydrochloric acid whereupon there precipitated a cream colored solid, which was washed with water and dried at 80°-85° C. to yield 52.6 g (88%) of 4-(2-fluorophenyl)-2,6-dimethyl-3,5-pyridinedicarboxylic acid, m.p. >285° C.

EXAMPLE 2

4-(2-Fluorophenyl)-2,6-dimethylpyridine

To 1400 ml of Dowtherm A heated to 240°-245° C. was added over a 10 minute period 113 g of 4-(2-fluorophenyl)-2,6-dimethyl-3,5-pyridinedicarboxylic acid and the reaction mixture was boiled for 50 minutes, cooled and allowed to stand at room temperature overnight. The crystalline solid, a by-product identified below, was filtered off and the filtrate was extracted with 700 ml of 3N hydrochloric acid followed by a second extraction with 300 ml of 3N hydrochloric acid. The combined acidic extracts were made basic by adding aqueous ammonium hydroxide and the alkaline mixture was extracted with 800 ml of chloroform. Evaporation of the chloroform yielded a brown mixture of solid and liquid, to which was added 300 ml of n-hexane and the mixture chilled. The solid was filtered off and dried. This solid, a by-product, was combined with the above noted solid by-product to yield 25.4 g (29%) of 2,4-dimethyl-5H-[1]benzopyrano[3,4-c]pyridin-5-one, m.p. 194°-197° C. The filtrate was concentrated to dryness on a steam bath, the residue taken up with ethanol and the solution concentrated on a rotary evaporator to yield, as a liquid, 55.2 g (70%) of 4-(2-fluorophenyl)-2,6-dimethylpyridine.

In another run as in the preceding paragraph using 113 g of 2-(2-fluorophenyl)-2,6-dimethyl-3,5-pyridinedicarboxylic acid, 1.1 liter of recovered Dowtherm A (used in a previous run) filtered through diatomaeous earth plus 300 ml of fresh of Dowtherm A, there was obtained 28.4 g (32%) of by-product, 2,4-dimethyl-5H-[1]benzopyrano[3,4-c]pyridin-5-one, m.p. 193°-196° C. and 44.8 g (57%) of 4-(2-fluorophenyl)-2,6-dimethylpyridine in free base form as a liquid.

In another run using a smaller proportionate amount of Dowtherm A, that is, 1200 ml, and 200 g of 4-(2-fluorophenyl-2,6-dimethyl-3,5-pyridinedicarboxylic acid, there was obtained a greater proportionate amount of said by-product, namely 57 g (36.7%) of 2,4-dimethyl-5H-[1]benzopyrano[3,4-c]pyridin-5-one and 42 g (30%) of 4-(2-fluorophenyl)-2,6-dimethylpyridine in free base form.

The above three batches of by-product, were combined, recrystallized from methanol and dried at 70°-75° C. to yield 141 g of 2,4-dimethyl-5H-[1]benzopyrano[,4-c]-pyridin-5-one, m.p. 204°-207° C.

The above three batches of 4-(2-fluorophenyl)-2,6-dimethylpyridine were combined and mixed well with 400 ml of n-hexane and 600 ml of 3N aqueous hydrochloric acid. The aqueous layer was separated, treated with decolorizing charcoal and concentrated to dryness on a rotary evaporator to give a white solid residue, about 9 g of which was recrystallized from isopropyl alcohol and dried over $P_2O_5$ at room temperature to yield 7.8 g of 4-(2-fluorophenyl)-2,6-dimethylpyridine hydrochloride hemihydrate, m.p. 200°-203° C. The remainder of the solid residue was dissolved in 700 ml of water, the solution made basic with aqueous ammonium hydroxide and the resulting alkaline solution extracted twice with 500 ml portions of chloroform. Removal of the chloroform yielded 148 g of 4-(2-fluorophenyl)-2,6-dimethylpyridine in free base form as a light brown liquid, which was used in the next step (Example 3).

EXAMPLE 3

4-(2-fluoro-5-nitrophenyl-2,6-dimethylpyridine

To 55 ml of concentrated sulphuric acid cooled in a salt-ice bath to about −10° to −15° C. was added 10.1 g of potassium nitrate over a 5 minute period. The mixture was allowed to stir for 10 minutes and then to it was added dropwise over a 30 minute period 18.5 g of 4-(2-fluorophenyl)-2,6-dimethylpyridine whereupon a gummy solid separated and a viscous slurry was obtained, the reaction temperature rising to about 0° C. In order to facilitate stirring, another 50 ml portion of concentrated sulphuric acid was added dropwise over a 15 minute period and the resulting mixture was stirred in the salt-ice bath and then stirred for a period of about 5 hours while allowing the temperature of the reaction mixture to rise to room temperature. The reaction mixture was poured onto a large excess of ice and the mixture was neutralized by adding aqueous ammonium hydroxide solution. The resulting light yellow fluffy precipitate was collected, washed with water and air dried. The solid was then dissolved in 300 ml of chloroform, the solution treated with decolorizing charcoal and filtered. The filtrate was concentrated on a rotary evaporator and the residue was slurred with 200 ml of 1:1 ether-n-hexane, the mixture filtered and the collected solid dried at 70°-75° C. to yield 18.67 g (84%) of 4-(2-fluoro-5-nitrophenyl)-2,6-dimethylpyridine, m.p. 169°-171° C.

EXAMPLE 4

A. 3-(2,6-dimethyl-4-pyridinyl)-4-fluorobenzeneamine 4-(2-fluoro-5-nitrophenyl)-2,6-dimethylpyridine, 180 g, was divided into four equal portions and each portion was reduced separately as follows. A mixture containing 45 g of 4-(2-fluoro-5-nitrophenyl)-2,6-dimethylpyridine, 200 ml of acetic acid and 800 mg of platinum dioxide was catalytically hydrogenated until hydrogen uptake ceased, about 4 hours with little hydrogen uptake the last thirty minutes. The catalyst was filtered off, washed with 300 ml of water, and the filtrate made basic by adding aqueous ammonium hydroxide. The solution was cooled to yield a oily material which solidified. The solid was collected, washed with water and dried to yield the desired amine. The remaining three 45 g portions of 4-(2-fluoro-5-nitrophenyl)-2,6-dimethylpyridine were reduced in the same way and the combined amine products were dissolved in 600 ml of concentrated hydrochloric acid and heated on a steam bath with stirring for 4 and ½ hours and then treated with decolorizing charcoal and filtered. The filtrate was made basic by adding aqueous ammonia and the resulting mixture was chilled to yield an oil which crystallized. The crystalline material was collected, washed with water and dried in an oven to yield 164.9 g of gummy solid. The solid was dissolved in ether containing 5% methanol and the solution was filtered through silica gel to remove the gummy impurities. The ether-methanol solvent of the filtrate was distilled off in vacuo and the residue was recrystallized from ether-isopropyl alcohol to yield 80.9 g of 3-(2,6-dimethyl-4-pyridinyl)-4-fluorobenzeneamine, m.p. 142°-145° C. Concentration of the mother liquor yielded another 43.4 g of the product, m.p. 141°-144° C., thereby giving a total yield of 82%.

B. Diethyl 4-fluoro-3-(2,6-dimethyl-4-pyridinyl)anilinomethylenemalonate

A mixture containing 122 g of 3-(2,6-dimethyl-4-pyridinyl)-4-fluorobenzeneamine, 130 g of diethyl ethoxymethylenemalonate and 120 ml of toluene was heated with stirring at 130°-135° C. for 3 and ½ hours using an air condenser allowing ethanol to escape from the reaction mixture. The reaction mixture was cooled and dissolved in one liter of boiling n-hexane. The hot solution was filtered through diatomaceous earth, the pad washed with hot n-hexane (400 ml), and the combined filtrate and washings were allowed to stand at room temperature for 18 hours. The white crystalline solid that separated was collected, washed with n-hexane and dried at 60°-65° C. to yield 159.6 g (74%) of diethyl 4-fluoro-3-(2,6-dimethyl-4-pyridinyl)anilinomethylenemalonate, m.p. 99°-100° C. Another 67 g of the crude product was obtained from the mother liquor and was cyclized without further purification as in the following Example 4C to yield 35.2 g of the product of Example 4C (m.p. >300° C.).

C. Ethyl 6-Fluoro-1,4-dihydro-7-(2,6-dimethyl-4-pyridinyl)-4-oxo-3-quinolinecarboxylate To a 1300 ml of boiling Dowtherm A in a two liter Erlenmeyer flask wrapped with aluminum foil (to maintain the temperature of the Dowtherm A at about 260°-265° C.) was added 154 g of diethyl 4-fluoro-3-(2,6-dimethyl-4-pyridinyl)anilinomethylenemalonate over a 5 minute period. The same reaction temperature was maintained for about 20 minutes and then the reaction mixture was allowed to cool. The precipitated tan solid was collected, washed successively with ether and ethanol and dried at 90°-95° C. to yield 107.4 g (79%) of ethyl 6-fluoro-1,4-dihydro-7-(2,6-dimethyl-4-pyridinyl)-4-oxo-3-quinolinecarboxylate, m.p. >300° C.

D. Ethyl 1-Ethyl-6-fluoro-1,4-dihydro-7-(2,6-dimethyl-4-pyridinyl)-4-oxo-3-quinolinecarboxylate A mixture containing 34 g of ethyl 6-fluoro-1,4-dihydro-7-(2,6-dimethyl-4-pyridinyl)-4-oxo-3-quinolinecarboxylate, finely divided anhydrous potassium carbonate and 250 ml of dimethylformamide was heated with stirring on a steam bath for 20 minutes and then 9 ml of ethyl iodide was added over a 20 minute period. The reaction mixture was heated on a steam bath with stirring for 2 and ½ hours and then concentrated to dryness on a rotary evaporator. The residue was shaken well with 300 ml of water and 500 ml of chloroform. The layers were separated and the aqueous layer was extracted with another 200 ml portion of chloroform. The combined chloroform extracts were concentrated in vacuo to remove the chloroform. The remaining solid was dissolved in 150 ml of hot isopropyl alcohol, the hot solution treated with decolorizing charcoal and filtered. The filtrate was concentrated on a rotary evaporator to a volume of about 50 ml which was diluted with ether until turbid. The mixture was allowed to cool and the separated crystalline solid was collected, washed with ether and dried at 80°-85° C. to yield 18.5 g of ethyl 1-ethyl-6-fluoro-1,4-dihydro-7-(2,6-dimethyl- 4-pyridinyl)-4-oxo-3-quinolinecarboxylate, m.p. 221°-224° C. Further concentration of the mother liquor yielded another 3.4 g (60%) of product, m.p. 220°-223° C. A larger run (0.3 mole scale) gave the above compound, m.p. 222°-225° C., in 80% yield.

E.

1-Ethyl-6-fluoro-1,4-dihydro-7-(2,6-dimethyl-4-pyridinyl)-4-oxo-3-quinolinecarboxylic Acid A mixture containing 98 g of ethyl 1-ethyl-6-fluoro-1,4-dihydro-7-(2,6-dimethyl-4-pyridinyl)-4-oxo-3-quinolinecarboxylate, 50 ml of 35% aqueous sodium hydroxide solution, 500 ml of water and 100 ml of methanol was refluxed with stirring for 90 minutes and the resulting brown solution was acidified with acetic acid whereupon a light yellow precipitate separated. The mixture was allowed to stand at room temperature for about 2 hours and the precipitate was collected, washed successively with water and ethanol and then dried at 90°-95° C. to yield 86.8 g (95%) of 1-ethyl-6-fluoro-1,4-dihydro-7-(2,6-dimethyl-4-pyridinyl)-4-oxo-3-quinolinecarboxylic acid, m.p. >310° C.

I claim:

1. The process which comprises heating 4-(2-fluorophenyl)-2,6-dimethyl-3,5-pyridinedicarboxylic acid to produce a mixture of 4-(2-fluorophenyl)-2,6-dimethylpyridine and 2,4-dimethyl-5H-[1]benzopyrano[3,4-c]pyridin-5-one, separating the components of said mixture, and nitrating the 4-(2-fluorophenyl)-2,6-dimethylpyridine thus obtained to produce 4-(2-fluoro-5-nitrophenyl)-2,6-dimethylpyridine.

2. The process which comprises heating 4-(2-fluorophenyl)-2,6-dimethyl-3,5-pyridinedicarboxylic acid to produce a mixture of 4-(2-fluorophenyl)-2,6-dimethylpyridine and 2,4-dimethyl-5H-[1]benzopyrano[3,4-c]pyridin-5-one and separating the components of the mixture.

3. A compound of the formula I

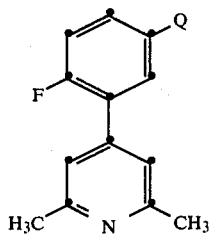

where Q is hydrogen, nitro, amino or NHCH=C(COOC$_2$H$_5$)$_2$, or acid-addition salt thereof.

4. 4-(2-Fluorophenyl)-2,6-dimethylpyridine according to claim 3 wherein Q is hydrogen.

5. 4-(2-Fluoro-5-nitrophenyl)-2,6-dimethylpyridine according to claim 3 wherein Q is nitro.

6. 3-(2,6-Dimethyl-4-pyridinyl)-4-fluorobenzeneamine according to claim 3 wherein Q is amino.

7. Diethyl 4-fluoro-3-(2,6-dimethyl-4-pyridinyl)anilinomethylenemalonate according to claim 3 wherein Q is NHCH=C(COOC$_2$H$_5$)$_2$.

* * * * *

UNITED STATES PATENT AND TRADEMARK OFFICE
CERTIFICATE OF CORRECTION

PATENT NO. : 4,699,984
DATED : October 13, 1987
INVENTOR(S) : Baldev Singh

It is certified that error appears in the above-identified patent and that said Letters Patent is hereby corrected as shown below:

```
Column 1, line 9, after "1984" insert: --, now abandoned--.

Column 2, line 40, "-one." should read -- -one,--.

Column 4, line 27, "ester" should read --ether--.

Column 5, line 14, "1-ethyl" should read --1-ethyl- --.
```

Signed and Sealed this

Second Day of August, 1988

Attest:

DONALD J. QUIGG

*Attesting Officer*   *Commissioner of Patents and Trademarks*